US00PP29943P2

(12) United States Plant Patent
Conibear

(10) Patent No.: US PP29,943 P2
(45) Date of Patent: Dec. 4, 2018

(54) LUPINE PLANT NAMED 'WCLBLSM'

(50) Latin Name: ***Lupinus* hybrid**
Varietal Denomination: WCLBLSM

(71) Applicant: Sarah Frances Conibear, Bideford (GB)

(72) Inventor: Sarah Frances Conibear, Bideford (GB)

( * ) Notice: Subject to any disclaimer, the term of this patent is extended or adjusted under 35 U.S.C. 154(b) by 0 days.

(21) Appl. No.: 15/731,492

(22) Filed: Jun. 19, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Anne Marie Grunberg
(74) *Attorney, Agent, or Firm* — C. A. Whealy

(57) ABSTRACT

A new and distinct cultivar of Lupine plant named 'WCLBLSM', characterized by its upright plant habit; moderately vigorous to vigorous growth habit; numerous large violet and white bi-colored flowers arranged on dense terminal racemes; and good garden performance.

2 Drawing Sheets

Botanical designation: *Lupinus* hybrid.
Cultivar denomination: 'WCLBLSM'.

BACKGROUND OF THE INVENTION

The present invention relates to a new and distinct cultivar of Lupine plant, botanically known as *Lupinus* hybrid and hereinafter referred to by the name 'WCLBLSM'.

The new Lupine plant is a product of a planned breeding program conducted by the Inventor in Devon, United Kingdom. The objective of the breeding program is to develop new uniform and freely flowering Lupine plants with large attractive flowers.

The new Lupine plant originated from an open-pollination in June, 2012 of an unnamed selection of *Lupinus* Russell Hybrids, not patented, as the female, or seed, parent with an unknown selection of *Lupinus* hybrid as the male, or pollen, parent. The new Lupine plant was discovered and selected by the Inventor in June, 2012 as a single flowering plant within the progeny of the stated open-pollination in a controlled environment in Devon, United Kingdom.

Asexual reproduction of the new Lupine plant by in vitro meristem culture in a controlled greenhouse environment in Hillegom, The Netherlands since March, 2013 has shown that the unique features of this new Lupine plant are stable and reproduced true to type in successive generations of asexual reproduction.

SUMMARY OF THE INVENTION

Plants of the new Lupine have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'WCLBLSM'. These characteristics in combination distinguish 'WCLBLSM' as a new and distinct Lupine plant:

1. Upright plant habit.
2. Moderately vigorous to vigorous growth habit.
3. Numerous large violet and white bi-colored flowers arranged on dense terminal racemes.
4. Good garden performance.

Plants of the new Lupine can be compared to plants of the female parent selection. Plants of the new Lupine differ from plants of the female parent selection primarily in the following characteristics:

1. Plants of the new Lupine are shorter than plants of the female parent selection.
2. Plants of the new Lupine are more vigorous and healthier than plants of the female parent selection.
3. Racemes of plants of the new Lupine are denser than racemes of plants of the female parent selection.

Plants of the new Lupine can be compared to plants of *Lupinus* hybrid 'The Pages', not patented. Plants of the new Lupine differ primarily from plants of 'The Pages' in the following characteristics:

1. Plants of the new Lupine are shorter than plants of 'The Pages'.
2. Plants of the new Lupine are more vigorous and healthier than plants of 'The Pages'.
3. Racemes of plants of the new Lupine are denser than racemes of plants of 'The Pages'.
4. Plants of the new Lupine and 'The Pages' differ in flower color as plants of 'The Pages' have pinkish red-colored flowers.

BRIEF DESCRIPTION OF THE PHOTOGRAPHS

The accompanying colored photographs illustrate the overall appearance of the new Lupine plant showing the colors as true as it is reasonably possible to obtain in colored reproductions of this type. Colors in the photographs may differ slightly from the color values cited in the detailed botanical description which accurately describe the colors of the new Lupine plant.

The photograph on the first sheet is side perspective view of a typical flowering plant of 'WCLBLSM' grown in a container.

The photograph on the second sheet is a close-up view of a typical flowering plant of 'WCLBLSM'.

DETAILED BOTANICAL DESCRIPTION

The aforementioned photographs and following observations, measurements and values describe plants of the new Lupine grown during the spring and early summer in 19-cm containers in an outdoor nursery in Hillegom, The Netherlands and under cultural practices typical of commercial Lupine production. During the production of the plants, day temperatures ranged from 15° C. to 27° C. and night temperatures ranged from 5° C. to 18° C. Plants were one year old when the photographs and the detailed description were taken. In the detailed description, color references are made to The Royal Horticultural Society Colour Chart, 2015 Edition, except where general terms of ordinary dictionary significance are used.

Botanical classification: *Lupinus* hybrid 'WCLBLSM'.

Parentage:

*Female, or seed, parent*.—Unnamed selection of *Lupinus* Russell Hybrids, not patented.

*Male, or pollen, parent*.—Unknown selection of *Lupinus* hybrid, not patented.

Propagation:

*Type*.—By in vitro meristem culture.

*Time to initiate roots, summer and winter*.—About four to five days at temperatures about 20° C.

*Time to produce a rooted young plant, summer*.—About five to six weeks at temperatures about 15° C. to 17° C.

*Time to produce a rooted young plant, winter*.—About seven to eight weeks at temperatures about 15° C. to 17° C.

*Root description*.—Thick, fleshy; typically creamy white to light brown in color, actual color of the roots is dependent on substrate composition, water quality, fertilizer type and formulation.

*Rooting habit*.—Main tap root with low lateral branching; medium in density.

Plant description:

*Plant and growth habit*.—Upright plant habit; moderately vigorous to vigorous growth habit and moderate growth rate.

*Branching habit*.—Freely basal branching habit.

*Plant height, soil level to top of foliar plane*.—About 43.1 cm.

*Plant height, soil level to top of floral plane*.—About 78 cm.

*Plant diameter* (*area of spread*).—About 57.4 cm.

Lateral branch description:

*Length*.—About 15 cm.

*Diameter*.—About 1.5 cm.

*Internode length*.—About 1.8 cm.

*Texture and luster*.—Sparsely to moderately pubescent; slightly glossy.

*Strength*.—Strong.

*Color*.—Close to 144B.

Leaf description:

*Arrangement*.—Alternate, palmately compound with about twelve leaflets per leaf.

*Leaf length*.—About 20.7 cm.

*Leaf width*.—About 20.9 cm.

*Leaflet length*.—About 12 cm.

*Leaflet width*.—About 3.9 cm.

*Leaf shape*.—Palmate, orbicular in outline.

*Leaflet shape*.—Oblanceolate.

*Leaflet apex*.—Acute.

*Leaflet base*.—Cuneate.

*Leaflet margin*.—Entire.

*Leaflet texture and luster, upper surface*.—Smooth, glabrous; matte.

*Leaflet texture and luster, lower surface*.—Moderately to densely pubescent; matte.

*Leaflet venation pattern*.—Pinnate.

*Leaflet color*.—Developing leaflets, upper surface: Close to N144C. Developing leaflets, lower surface: Close to 143C. Fully expanded leaflets, upper surface: Close to NN137A; venation, close to 143B. Fully expanded leaflets, lower surface: Close to between 138A and 191A; venation, close to 144A.

*Leaf petioles*.—Length: About 21.3 cm. Diameter: About 5 mm. Texture and luster, upper and lower surfaces: Moderately pubescent; matte. Color, upper surface: Close to 144B; proximally, tinged with close to 187B to 187D. Color, lower surface: Close to 144B.

*Stipules*.—Quantity and arrangement: One at the base of the petiole. Length: About 3.7 cm. Width: About 6 mm. Shape: Lanceolate. Color, upper and lower surfaces: Close to 144A to 144B tinged with close to 187B to 187C.

Flower description:

*Flower appearance and arrangement*.—Single large papilionaceous flowers arranged in dense terminal racemes; freely flowering habit with usually about 250 flowers developing per inflorescence; flowers face mostly outwardly.

*Natural flowering season*.—Continuous flowering from early summer into the midsummer in The Netherlands.

*Flower longevity*.—Flowers last about two weeks on the plant; flowers not persistent.

*Fragrance*.—Moderately fragrant; peppery.

*Inflorescence height*.—About 51 cm.

*Inflorescence diameter*.—About 7.5 cm.

*Flower diameter*.—About 2 cm by 2.3 cm.

*Flower length* (*height*).—About 2.1 cm.

*Flower buds*.—Length: About 1.6 cm. Diameter: About 6 mm. Shape: Ovate. Color: Base, close to 145B; proximally, close to 102C and 116B; distally, close to 145C.

*Petals*.—Quantity per flower: Flowers papilionaceous with an upper standard petal, two lateral (wing) petals and a lower keel petal. Length: Upper standard petal: About 2 cm. Lateral petals: About 2.1 cm. Keel: About 1.5 cm. Width: Upper standard petal: About 2 cm. Lateral petals: About 1.3 cm. Keel: About 5 mm. Shape: Upper standard petal: Orbicular; concave. Lateral petals: Obovate; curved and concave. Keel: Ovate; curved and folded. Apex: Upper standard petal: Rounded with very short apiculate apex. Lateral petals: Obtuse. Keel: Caudate. Margin, all petals: Entire. Texture and luster, upper and lower surfaces, all petals: Smooth, glabrous; matte. Color, when opening, upper surface: Upper standard petal: Close to 157D; towards the base, close to 96B; small basal blotch, close to 203A. Lateral petals: Close to 90D. Keel: Close to lighter than 157D; apex, close to 203C. Color, when opening, lower surface: Upper standard petal: Close to 157D; towards the base, close to 95C. Lateral petals: Close to 88B. Keel: Close to lighter than 157D; apex, close to 203C. Color, fully opened, upper surface: Upper standard petal: Close to NN155B; towards the base and margins, close to N89C to N89D; small basal blotch, close to 203A; with development, ground color becoming closer to NN155C and towards the base and margins color becoming closer to 95C. Lateral petals: Close to 91A; venation, close to 90C; with development, ground color becoming closer to 93B. Keel: Close to 91D; apex, close to 203C; color does not change with development. Color, fully opened, lower surface: Upper standard petal: Close to NN155C; towards the base and margins, close to N89C to N89D. Lateral petals: Close to between N88A and N89B. Keel: Close to 91D; apex, close to 203C.

*Sepals*.—Quantity per flower: Two. Length: About 7 mm. Width: About 4 mm to 5 mm. Shape: Ovate; concave. Apex: Narrowly acute. Base: Cuneate. Margin: Entire. Texture and luster, upper and lower surfaces: Densely pubescent; slightly glossy. Color: When opening, upper and lower surfaces: Close to 145B. Fully opened, upper surface: Close to 145A to 145B. Fully opened, lower surface: Close to 145B.

*Peduncles*.—Length: About 48.5 cm. Diameter: About 1.3 cm. Strength: Strong. Aspect: Mostly erect. Texture: Smooth, glabrous. Color: Close to 146D tinged with close to 68C.

*Pedicels*.—Length: About 1 cm. Diameter: About 1.5 mm. Strength: Moderately strong. Aspect: About 70° from peduncle axis Texture: Smooth, glabrous. Color: Close to 147D.

*Reproductive organs*.—Androecium: Quantity per flower: About ten. Filament length: About 3 mm to 9 mm. Filament color: Close to 145B. Anther length: About 0.5 mm to 3.5 mm. Anther shape: Narrowly oblong. Anther color: Close to 24A. Amount of pollen: Moderate. Pollen color: Close to 24A. Gynoecium: Quantity per flower: One. Pistil length: About 1 cm. Style length: About 9 mm. Style color: Close to 145B. Stigma shaped: Club-shaped, fringed. Stigma color: Close to 20B. Ovary color: Close to 145B to 145C.

*Fruits and seeds*.—Fruit and seed development has not been observed on plants of the new Lupine to date.

Garden performance: Plants of the new Lupine have been observed to have good garden performance and to tolerate rain, wind, high temperatures of about 35° C. and to be hardy to USDA Hardiness Zone 5.

Pathogen & pest resistance: Plants of the new Lupine have not been observed to be resistant to pathogens and pests common to Lupine plants.

It is claimed:

1. A new and distinct Lupine plant named 'WCLBLSM' as illustrated and described.

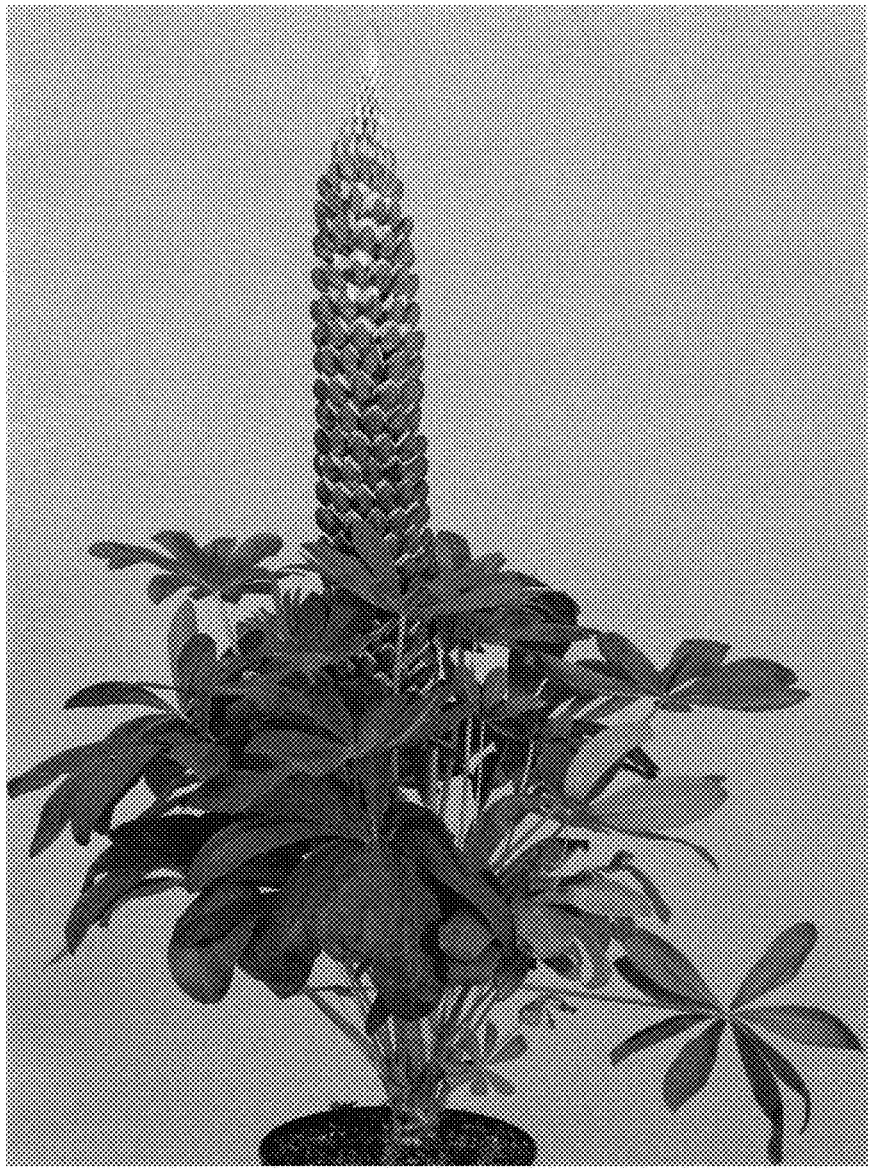

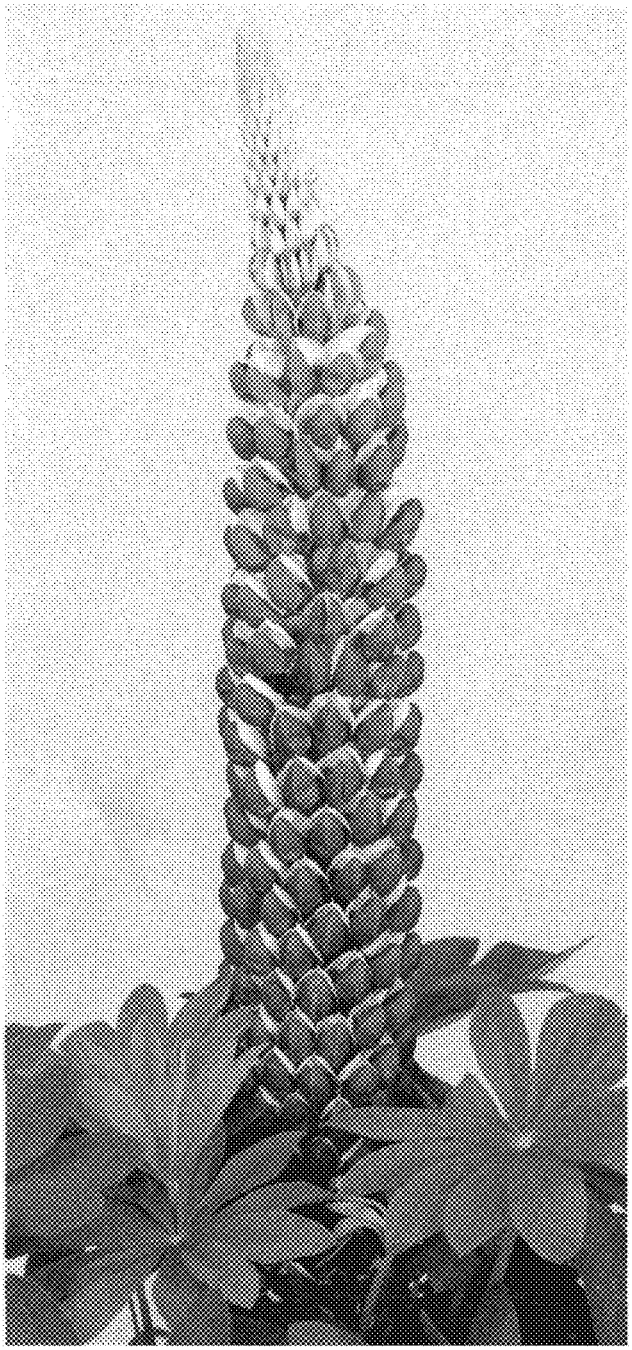

* * * * *